United States Patent [19]

Sims et al.

[11] Patent Number: 5,164,398

[45] Date of Patent: Nov. 17, 1992

[54] IBUPROFEN-ANTITUSSIVE COMBINATIONS

[75] Inventors: Robert T. Sims, Holicong; William Slivka, Philadelphia, both of Pa.

[73] Assignees: Merck & Co., Inc., Rahway, N.J.; McNeil-PPC, Inc., Fort Washington, Pa.

[21] Appl. No.: 678,772

[22] Filed: Apr. 1, 1991

[51] Int. Cl.$^5$ ............... A61K 31/19; A61K 31/44
[52] U.S. Cl. .................. 514/282; 514/295; 514/570
[58] Field of Search .......... 514/570, 282, 295

[56] References Cited

U.S. PATENT DOCUMENTS

| | | | |
|---|---|---|---|
| 4,571,400 | 2/1986 | Arnold | 514/282 |
| 4,738,966 | 4/1988 | Sunshine et al. | 514/277 |
| 4,839,176 | 1/1989 | Pankhania et al. | 424/465 |
| 4,844,907 | 7/1989 | Elger et al. | 424/465 |
| 4,851,444 | 7/1989 | Sunshine et al. | 514/570 |
| 4,877,620 | 10/1989 | Loew et al. | 424/451 |
| 4,920,149 | 4/1990 | Sunshine et al. | 514/557 |

FOREIGN PATENT DOCUMENTS

| | | |
|---|---|---|
| 0388125 | 9/1990 | European Pat. Off. |
| WO85/04589 | 10/1985 | PCT Int'l Appl. |

OTHER PUBLICATIONS

S. A. Cooper et al., "Analgesic Efficacy of a Ibuprofen-Codeine Combination", *Pharmacotherapy*, 2, 162 (1982).

*Primary Examiner*—S. J. Friedman
*Attorney, Agent, or Firm*—Melvin Winokur; Joseph F. Brindisi; Joseph F. DiPrima

[57] ABSTRACT

This invention relates to pharmaceutical compositions for use in the treatment of pain and inflammation and the relief of cough and cold symptoms in a mammalian organism, said composition comprising:

(i) an analgesically and anti-inflammatory effective amount of (S)-ibuprofen, or a salt thereof, substantially free of (R)-ibuprofen; and (ii) an antitussively effective amount of at least one antitussive agent selected from codeine, hydrocodone, caramiphen, carbetapentane, or dextromethorphan, or a therapeutically active stereoisomer thereof substantially free of its other stereoisomers and optionally iii) a therapeutically effective amount of at least one expectorant selected from guaicolsulfonate, guaifenesin, guaiacol, or terpin;

or a pharamceutically acceptable salt thereof.

9 Claims, No Drawings

IBUPROFEN-ANTITUSSIVE COMBINATIONS

BACKGROUND OF THE INVENTION

The non-steroidal anti-inflammatory drugs (NSAID) have been utilized in the treatment of pain/inflammation and have been disclosed as useful in the treatment, management and mitigation of cold symptoms and the pain associated therewith.

Ibuprofen (2-(4-isobutylphenyl)propionic acid) is a well known and commonly employed NSAID. Recently, it has been found that a faster onset of pain relief and an enhanced analgesic response can be obtained by the utilization of the single enantiomer (S)-ibuprofen in comparison to racemic ibuprofen, (see for example U.S. Pat. No. 4,877,620).

Antitussives (cough suppressants) are useful in relieving cough symptoms associated with cold and flu conditions. Expectorants are useful in relieving upper chest congestion associated with the common cold and flu.

Combinations of ibuprofen with antitussives have been disclosed, however despite the fact that the cold/pain sufferer is in need of quick and enhanced relief there has been no consideration given to the employment of (S)-ibuprofen, or a salt thereof, in combination with an antitussive for the treatment of pain and the relief of cough, cold symptoms.

DETAILED DESCRIPTION OF THE INVENTION

This invention relates to pharmaceutical compositions for use in the treatment of pain and inflammation and the relief of cough and cold symptoms in a mammalian organism, said composition comprising:
  (i) an analgesically and anti-inflammatory effective amount of (S)-ibuprofen, or a salt thereof, substantially free of (R)-ibuprofen; and
  (ii) an antitussively effective amount of at least one antitussive agent selected from codeine, hydrocodone, caramiphen, carbetapentane, or dextromethorphan, or a therapectically active stereoisomer thereof substantially free of its other stereoisomers and optionally
  iii) a therapeutically effective amount of at least one expectorant selected from guaicolsulfonate, guaifenesin, guaiacol, or terpin;
or a pharmaceutically acceptable salt thereof.

This invention is also directed to a method of treating pain and inflammation and the relief of cough and cold symptoms in a mammalian organism in need of such treatment comprising administering to such organism:
  (i) an analgesically and anti-inflammatory effective amount of (S)-ibuprofen, or a salt thereof, substantially free of (R)-ibuprofen; and
  (ii) an antitussively effective amount of at least one antitussive agent selected from codeine, hydrocodone, caramiphen, carbetapentane, or dextromethorphan, or a therapeutically active steroisomer thereof substantially free of its other stereoisomers; and optionally
  iii) a therapeutically effective amount of at least one expectorant selected from guaicolsulfonate, guaifenesin, guaiacol, or terpin;
or a pharmaceutically acceptable salt thereof.

This invention is also directed to a method of eliciting an onset hastened and enhanced response for the treatment of pain and inflammation and the relief of cough and cold symptoms in a mammalian organism in need of such treatment comprising administering to such organism:
  (i) an analgesically and anti-inflammatory effective amount of (S)-ibuprofen, or a salt thereof, substantially free of (R)-ibuprofen; and
  (ii) an antitussively effective amount of at least one antitussive agent selected from codeine, hydrocodone, caramiphen, carbetapentane or dextromethorphan, or a therapeutically active stereoisomer thereof substantially free of its other stereoisomers; and optionally
  iii) a therapeutically effective amount of at least one expectorant selected from guaicolsulfonate, guaifenesin, guaiacol, or terpin;
or a pharmaceutically acceptable salt thereof.

The compositions and methods of the present invention may be used to treat pain and inflammation, or pain alone or inflammation alone where only one is present, along with the treatment of cough and cold symptoms.

Substantially free of (R)-ibuprofen should be taken to mean that the ratio of (S)-ibuprofen to (R)-ibuprofen is at least 90:10. Substantially free with respect to an antitussive stereoisomer should be taken to mean that the ratio of that stereoisomer to all other stereoisomers of the antitussive is at least 90:10.

Salts of (S)-ibuprofen include salts with alkali metals, such as sodium or potassium, salts with alkaline earth metals, such as calcium, or salts with other metals such as magnesium, aluminum, iron, zinc, copper, nickel or cobalt.

Salts of (S)-ibuprofen further include the amino acid salts, particularly the basic amino acids such as lysine or arginine. Specifically included within the above composition is (S)-ibuprofen-(S)-lysine and (S)-ibuprofen-(R)-lysine.

Salts of the antitussive include but are not limited to the phosphate, sulfate, bitartrate, hydrochloride, hydrobromide, edisylate, citrate and tannate.

(S)-ibuprofen may be prepared following the procedures disclosed in U.S. Pat. No. 4,877,620. Metal salts of ibuprofen may be obtained by contacting a hydroxide, or carbonate with ibuprofen. Amino acid salts of ibuprofen may be obtained by contacting an amino acid in solution with ibuprofen.

The utilization of (S)-ibuprofen in an analgesic/antitussive combination offers significant advantages over the combination of racemic ibuprofen with an antitussive. (S)-ibuprofen provides a faster onset of pain relief and an enhanced degree of relief compared to racemic ibuprofen. These benefits are increased in an (S)-ibuprofen/antitussive combination as the antitussive may potentiate the action of (S)-ibuprofen. This has not heretofore been observed because the art has not proposed the combination of the (S)-ibuprofen enantiomer, absent (R)-ibuprofen, with an antitussive. Furthermore the antitussive also may potentiate the duration of the analgesic and anti-inflammatory response. The presence of the (R)-ibuprofen may blur the potentiated effect.

Furthermore, the absence of (R)-ibuprofen provides significant benefits particularly to the subject in the weakened state of a cold, flu, or cough condition. The allergic contraindications sometimes associated with ibuprofen administration, and which may be particularly detrimental to the cold/flu/cough sufferer, may be absent or reduced in a composition wherein the (R)-ibuprofen is absent. Furthermore, the subject will no longer need to divert metabolic energy to the inversion of the (R)-enantiomer or the removal of this enantiomer.

The absence of inversion reduces or eliminates the formation and incorporation into fatty tissue of hybrid-ibuprofen containing triglycerides. The renal burden and renal toxicities sometimes associated with ibuprofen therapy are reduced or absent in a substantially (R)-ibuprofen free composition.

The absence of inactive enantiomers, particularly (R)-ibuprofen provides for significant size and weight advantages in a combination dosage form, particularly a sustained release dosage form. Where a sustained release dosage of ibuprofen may have required 800 to 1000 mg, the employment of (S)-ibuprofen reduces, the weight to 650 to 800 mg, and provides for a more practical size tablet for an ibuprofen/antitussive combination.

An effective amount of (S)-ibuprofen, or a salt thereof, for use in an unit dose composition of this invention may range from 50 to 800 mg (S)-ibuprofen. The preferred amount of (S)-ibuprofen is about 100 to 400 mg. The amount of a salt such as (S)-ibuprofen-(S)-lysine is determined based on the amount of (S)-ibuprofen contained therein. The antitussive employed herein is selected from codeine, hydrocodone, carbetapentane, caramiphen, and dextromethorphan, or a therapeutically active stereoisomer thereof substantially free of its other stereoisomers, or a pharmaceutically acceptable salt thereof.

The amount of antitussive useful in the practice of the present invention may vary from about 1 mg to 50 mg depending on the specific antitussive. The amount of a salt such as codeine phosphate is determined based on the amount of antitussive contained therein. The amount of expectorant useful in the practice of the present invention may vary from about 100 mg to 1000 mg per daily dosage.

The present compositions may be administered in the form of tablets, capsules, elixirs, syrups, drops, granules, liquids, nasal spray inhaler or a suspension. For oral administration the active components may be admixed with a pharmaceutically acceptable diluent such as lactose, starch, sucrose, cellulose, magnesium stearate, dicalcium phosphate, calcium sulfate, mannitol and in a liquid composition, ethyl alcohol. Acceptable binders such as PVP, starch, gelatin, natural sugars, corn sweeteners, natural and synthetic gums such as acacia, sodium alginate, carboxymethylcellulose, polyethylene glycol and waxes, may also be admixed with the active components. Where necessary lubricants such as magnesium stearic acid talc, and disintegrators such as starch, methylcellulose, agar, bentonite and guar gum and super disintegrators such as docusate sodium, starch glycollate or cross linked PVP may also be included.

The active components may also be formulated in sustained release formulations. These formulations may be employed in oral, dermal, rectal or vaginal administrations. Such sustained release forms also include layered formulations which provide for distinct release ratio and thus may be more beneficial in allowing for short and long term relief.

The following examples illustrate the compositions of the present invention and as such are not to be considered as limiting the invention set forth in the claims appended hereto.

EXAMPLE 1

| (S)-ibuprofen-(S)-lysine, Antitussive Tablet | |
|---|---|
| (S)-ibuprofen-(S)-lysine | 342 mg |
| Codeine phosphate | 30 mg |
| PVP | 15 mg |
| Avicel PH101 | 40 mg |
| Magnesium Stearate | 4 mg |

EXAMPLE 2

| (S)-ibuprofen-(S)-lysine, Antitussive Sustained Release | |
|---|---|
| (S)-ibuprofen-(S)-lysine | 685 mg |
| Codeine phosphate | 100 mg |
| PVP | 30 mg |
| Avicel PH101 | 80 mg |
| Magnesium Stearate | 8 mg |
| Methocel E10MCR | 66 mg |
| Methocel K100MLV | 200 mg |

EXAMPLE 3

| (S)-ibuprofen-(S)-lysine/antitussive elixir | |
|---|---|
| (S)-ibuprofen-(S)-lysine | 342 mg |
| Codeine phophate | 12 mg |
| q.s. syrup | 5 ml |

EXAMPLE 4

| (S)-ibuprofen-(S)-lysine, Antitussive Tablet | |
|---|---|
| (S)-ibuprofen-(S)-lysine | 342 mg |
| Dextromethorphan hydrobromide | 15 mg |
| PVP | 15 mg |
| Avicel PH101 | 40 mg |
| Magnesium Stearate | 4 mg |

EXAMPLE 5

| (S)-ibuprofen-(S)-lysine, Antitussive Sustained Release | |
|---|---|
| (S)-ibuprofen-(S)-lysine | 685 mg |
| Dextromethorphan hydrobromide | 30 mg |
| PVP | 30 mg |
| Avicel PH101 | 80 mg |
| Magnesium Stearate | 8 mg |
| Methocel E10MCR | 66 mg |
| Methocel K100MLV | 200 mg |

EXAMPLE 6

| (S)-ibuprofen-(S)-lysine/antitussive elixir | |
|---|---|
| (S)-ibuprofen-(S)-lysine | 342 mg |
| Dexttromethorphan hydrobromide | 5 mg |
| q.s. syrup | 5 ml |

EXAMPLE 7

| (S)-ibuprofen-(S)-lysine, Antitussive Sustained Release | |
|---|---|
| (S)-ibuprofen | 400 mg |

-continued

| (S)-ibuprofen-(S)-lysine, Antitussive Sustained Release | |
| --- | --- |
| Codeine phosphate | 100 mg |
| PVP | 30 mg |
| Avicel PH101 | 80 mg |
| Magnesium Stearate | 8 mg |
| Methocel E10MCR | 66 mg |
| Methocel K100MLV | 200 mg |

What is claimed is:

1. A pharmaceutical composition for use in the treatment of pain and inflammation and the relief of cough and cold symptoms in a mammalian organism and adapted for unit dosage oral administration said composition comprising:
   (i) an analgesically and anti-inflammatory effective amount of (S)-ibuprofen, or a salt thereof, substantially free of (R)-ibuprofen; and
   (ii) an antitussively effective amount of at least one antitussive selected from codeine, hydrocodone, dextromethorphan or a therapeutically active stereoisomer thereof substantially free of its other stereoisomers.

2. A composition of claim 1 where the ibuprofen is present as the salt (S)-ibuprofen-(S)-lysine, or (S)-ibuprofen-(R)-lysine.

3. A composition of claim 2 comprising from about 50 to 800 mg of (S)-ibuprofen.

4. A composition of claim 3 wherein the antitussive is codeine or dextromethorphan or a pharmaceutically acceptable salt thereof.

5. A composition of claim 4 wherein the expectorant is guaifenesin.

6. A method of eliciting an onset hastened and enhanced response for the treatment of pain and inflammation and the relief of cough and cold symptoms in a mammalian organism in need of such treatment comprising administering to such organism.
   (i) an analgesically and anti-inflammatory effective amount of (S)-ibuprofen, or a salt thereof, substantially free (R)-ibuprofen; and
   (ii) an antitussively effective amount of at least one antitussive agent selected from codeine, hydrocodone, dextromethorphan or a therapeutically active stereoisomer thereof substantially free of its other stereoisomers.

7. A method of reducing the side effects associated with the administration of an ibuprofen/antitussive combination which comprises the administration of (S)-ibuprofen or a salt thereof, substantially free of (R)-ibuprofen, and at least one antitussive agent selected from codeine, hydrocodone, dextromethorphan or a therapeutically active stereoisomer thereof substantially free of its other stereoisomers, or a pharmaceutically acceptable salt thereof.

8. A method of reducing the size and weight of an ibuprofen/antitussive combination dosage form which comprises combining (S)-ibuprofen, or a salt thereof, substantially free of (R)-ibuprofen and at least one antitussive agent selected from codeine, hydrocodone, dextromethorphan or a therapeutically active stereoisomer thereof substantially free of its other stereoisomers, or a pharmaceutically acceptable salt thereof.

9. A composition of claim 3 wherein the antitussive is hydrocodone or dextromethorphan or a pharmaceutically acceptable salt thereof.

* * * * *